United States Patent
Jackson et al.

(10) Patent No.: US 7,459,584 B2
(45) Date of Patent: Dec. 2, 2008

(54) PROCESS FOR THE PREPARATION OF LACTIC ACID AND GLYCERIC ACID

(75) Inventors: James E. Jackson, Haslett, MI (US); Dennis J. Miller, Okemos, MI (US); Simona Marincean, Dewitt, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 447 days.

(21) Appl. No.: 11/232,833

(22) Filed: Sep. 22, 2005

(65) Prior Publication Data

US 2007/0066844 A1    Mar. 22, 2007

(51) Int. Cl.
*C07C 51/00*    (2006.01)
(52) U.S. Cl. .................................................... 562/515
(58) Field of Classification Search ........................ None
See application file for complete search history.

(56) References Cited

U.S. PATENT DOCUMENTS

| 2,024,565 | A | 12/1935 | Braun |
| 2,382,889 | A | 8/1945 | Lock |
| 2003/0155298 | A1 | 8/2003 | Cockrem |

OTHER PUBLICATIONS

Buhler et al, Journal of the American Chemical Society, Epimerization and Fragmentation of Glucose by Quaternary Ammonium Base Type Anion Exchange Resins, 1955, 77, pp. 481-482.*
Bruijn, J.M., et al., Int. Sugar 101-104 (1994).
Ellis, A.V., et al., J. Org. Chem. 67, 8469-8474 (2002).
Bruijn, J.M., et al., Recl. Trav. Chim. Pays-Bas 106, 35-43 (1987).
Bruijn, J.M., et al., Sugar Technology Review 13 21-52 (1986).

* cited by examiner

*Primary Examiner*—Paul A Zucker
(74) *Attorney, Agent, or Firm*—Ian C. McLeod

(57) ABSTRACT

Hexose and pentose monosaccharides are degraded to lactic acid and glyceric acid in an aqueous solution in the presence of an excess of a strongly anionic exchange resin, such as AMBERLITE IRN78 and AMBERLITE IRA400. The glyceric acid and lactic acid can be separated from the aqueous solution. Lactic acid and glyceric acid are staple articles of commerce.

15 Claims, 1 Drawing Sheet

PROCESS FOR THE PREPARATION OF LACTIC ACID AND GLYCERIC ACID

STATEMENT REGARDING GOVERNMENT RIGHTS

This invention was funded under Department of Energy Grant No. DE-AC06-76RL01830. The U.S. Government has certain rights to this invention.

CROSS-REFERENCE TO RELATED APPLICATIONS

None

STATEMENT REGARDING FEDERALLY SPONSORED RESEARCH OR DEVELOPMENT

Not Applicable

BACKGROUND OF THE INVENTION (1) Field of the Invention

The present invention relates to the cleavage of hexose or pentose monosaccharides selectively to three (3) carbon products, primarily lactic acid and glyceric acid. C5 pentose monosaccharides can produce acetic acid and glycolic acid as well. In particular, the present invention relates to the production, isolation and purification of lactic acid and glyceric acid using a solid base catalyst such as an anionic ion exchange resin at ambient pressures.

(2) Description of the Related Art

The prior art describes the separation of lactic acid from other acid impurities as evidenced by US2003/0155298 which is incorporated by reference herein. There is no prior art relative to the selective cleavage of a hexose or pentose monosaccharide to a C3 or C2 product using a strongly basic solid base such as an anionic ion exchange resin. The prior art uses water soluble bases; however, the yields of lactic acid are less than 60% (Bruijn, J. M., et al., Int. Sugar 101-104 (1994); Ellis, A. V., et al., J. Org. Chem. 67, 8469-8474 (2002); Bruijn, J. M., et al., Recl. Trav. Chim. Pays-Bas 106, 35-43 (1987); U.S. Pat. No. 2,382,889 to Lock; U.S. Pat. No. 2,024,556 to Braun; and Bruijn, J. M., et al., Sugar Technology Review 13 21-52 (1986)). The prior art also uses hydrogenolysis to convert the sugar alcohols of hexoses and pentoses (200° C., 1000 psi $H_2$, metal catalyst and a base) which are difficult and expensive conditions. There is a need for an improved process.

OBJECTS

It is therefore an object of the present invention to provide a novel chemical process for the selective cleavage of a hexose or pentose monosaccharide selectively into C3 products, particularly lactic acid and glyceric acid. It is further an object of the present invention to provide a process which is easily performed and which is economical. These and other objects will become increasingly apparent from the following description and the claims.

SUMMARY OF THE INVENTION

The present invention relates to a process for the preparation and purification of lactic acid and glyceric acid in an aqueous solution which comprises:

(a) reacting an aqueous hexose or pentose sugar solution with a solid base at a temperature at least about 30° C. to produce anions of lactic acid and glyceric acid bound to the solid base and unreacted sugars and byproducts in the solution;

(b) separating the unreacted sugars and byproducts in the solution from the bound lactic acid and glyceric acid anions; and (c) contacting the bound lactic acid and glyceric acid anions on the solid base with an aqueous acid solution to produce the lactic acid and glyceric acid in the aqueous solution. The solid base can be inorganic or organic and generally has a pKa of about 14.

The present invention particularly relates to a process for the preparation and purification of predominantly lactic acid and glyceric acid in an aqueous solution which comprises: (a) reacting an aqueous hexose sugar solution with a basic anionic exchange resin at a temperature between about 30° and 60° C. to produce anions of lactic acid and glyceric acid bound to the anionic ion exchange resin and unreacted sugars and byproducts in the solution; (b) separating the unreacted sugars and byproducts in the solution from the bound lactic acid and glyceric acid anions; and (c) contacting the bound lactic acid and glyceric acid anions on the anionic exchange column with an aqueous acidic solution to produce purified lactic acid and glyceric acid in the aqueous solution.

Scheme 1 shows the likely steps leading to lactic acid from fructose or glucose as hexose sugars.

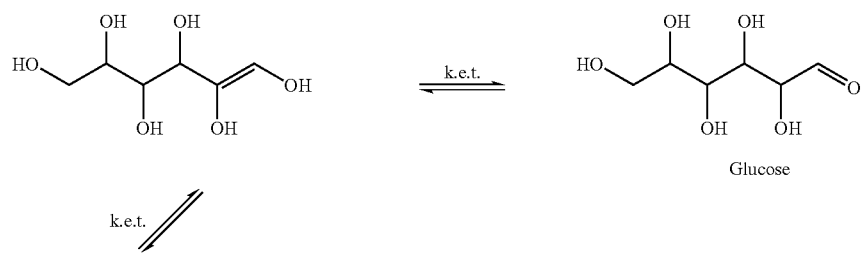

Scheme 1. Mechanism of base-catalyzed sugar cleavage to glyceraldehydes and subsequent base-catalyzed rearrangement to form lactate.

-continued
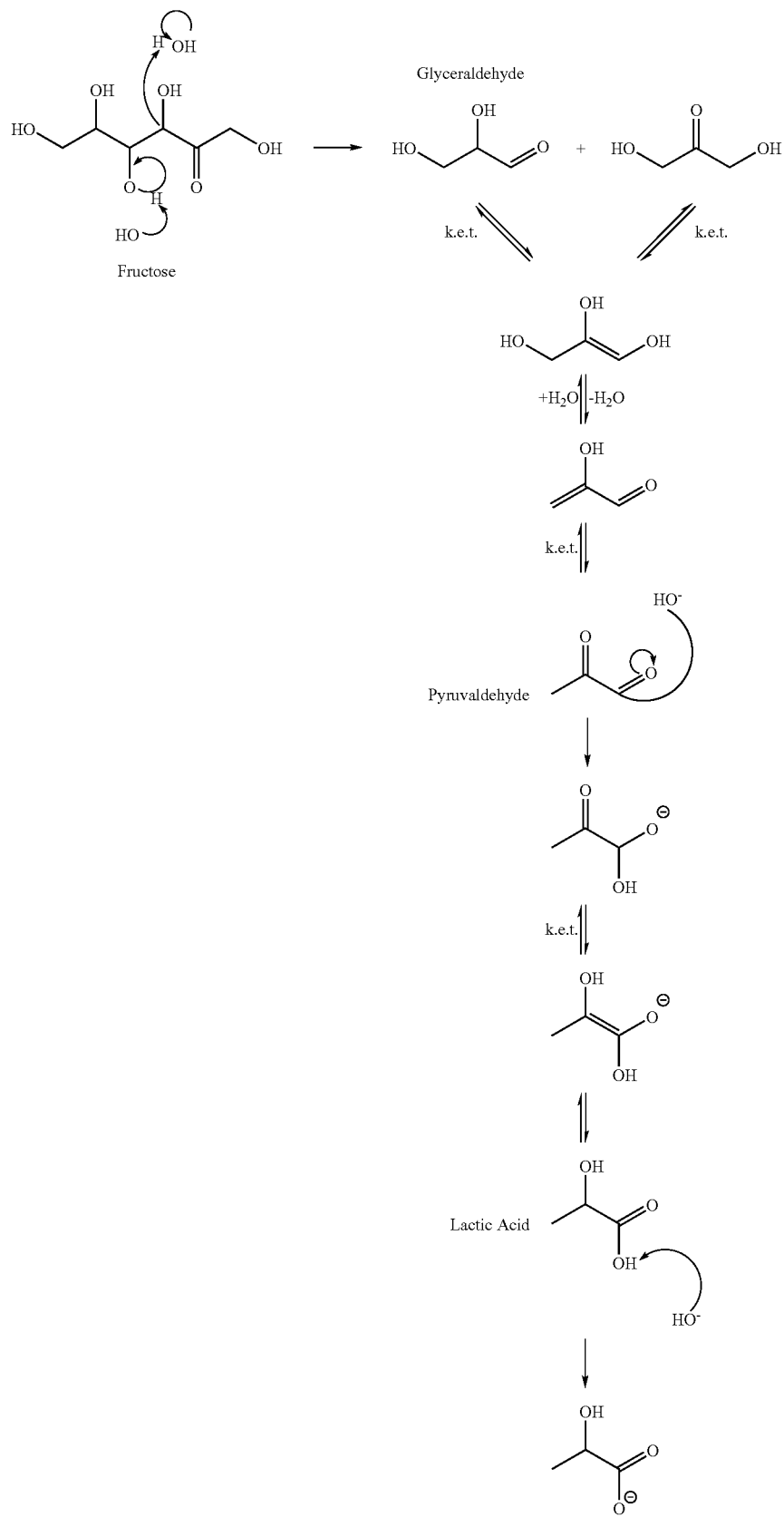

However, the Applicant does not want to be bound by any particular theory.

Preferably the process is performed at atmospheric pressures. Preferably the hexose sugar is glucose and/or fructose. The pentose sugars are preferably xylose and arabinose. Preferably the temperature is 50° C. Preferably the resin is an anion exchange polystyrene divinylbenzene cross-linked resin. Preferably a molar excess of resin at 2 moles of hydroxyl sites per mole of sugar is reacted. Preferably the process is continuous with three (3) columns, one for the reaction, one for lactic acid and glyceric acid separation in step (b) and optionally in step (a) one for regeneration of the resin or other solid base for reuse. Preferably the process is in a sealed vessel.

The preferred anionic ion exchange resin is a basic polystyrene/divinylbenzene cross-linked resin with a quaternary ammonium functionality, which are in the AMBERLITE series, for example, of resins. Preferably the quaternary ammonium compound has a tetraalkylammonium hydroxide functionality. Also AMBERLITE resins, IRA402, 458, 900, 958, IRN78 are strong basic anionic resins. Numerous other solid bases both inorganic and organic can be used particularly, the hydrotalcites, natural or synthetic and other strongly metal base oxides.

The substance and advantages of the present invention will become increasingly apparent by reference to the following drawings and the description.

DESCRIPTION OF THE PREFERRED EMBODIMENTS

Figure 1:
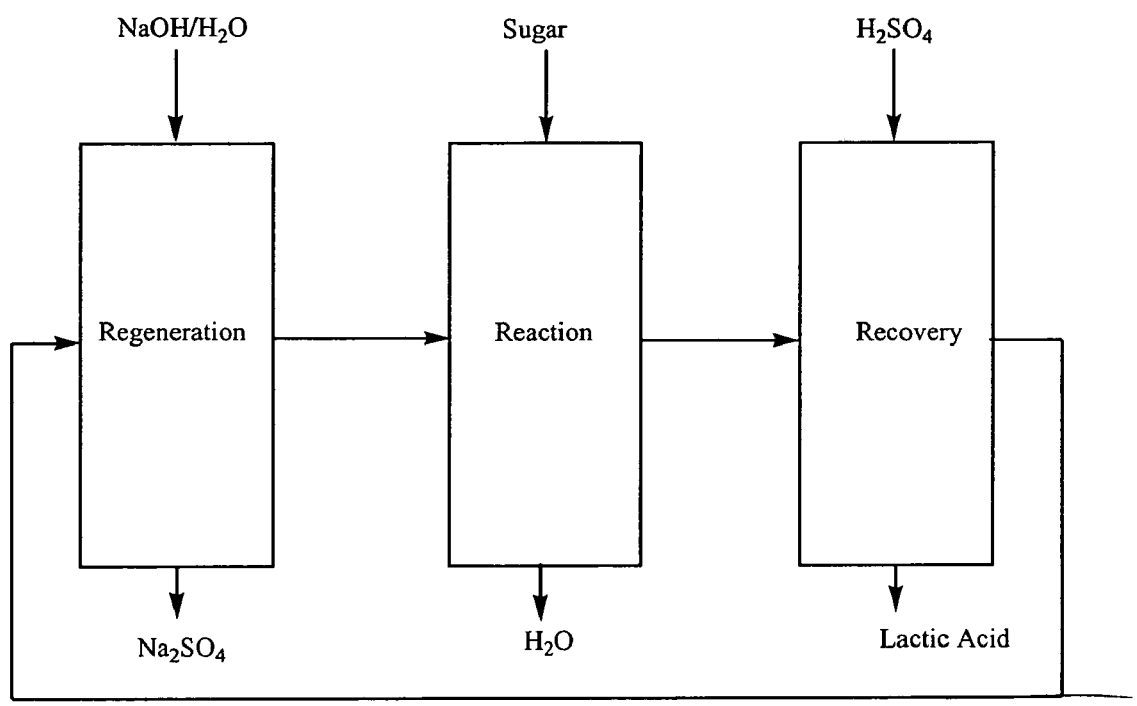
FIG. 1 is a schematic view of the continuous process with acid generation and recovery with resin catalyst regeneration.

The present invention preferably provides selective cleavage of sugars such as glucose and fructose in the presence of strongly anionic exchange resins such as AMBERLITE IRN78, and AMBERLITE IRA400. The major products of the cleavage of fructose and glucose are organic compounds with three carbons (C3), lactic acid (2-hydroxypropionic acid), glyceric acid (2,3-dihydroxypropionic acid), glyceraldehyde (2,3-dihydroxypropanal), pyruvaldehyde (2-oxopropanal), propylene glycol (1,2-propanediol), and glycerol (1,2,3-propanetriol). The major acid products of arabinose and xylose and lactic acid, glyceric acid, acetic acid and glycolic acid.

The basic anionic resins catalyze the selective cleavage of the C3-C4 bond of fructose, where the major product is lactic acid. The conditions are extremely mild (50° C. and atmospheric pressure) as opposed to the ones corresponding to classic hydrogenolysis (200° C., 1000 psi $H_2$, metal catalyst, and base). Also the selectivity to C3 products is larger in the presence of the basic resins or other solid bases (by hydrolysis). When the resin to glucose molar ratio is at least 2, at 50° C. and atmospheric pressure, the major products are lactic acid and glyceric acid and essentially all the other products also have three-carbon backbones (C3) which was unexpected. The stoichiometric ratio includes two moles of resin $OH^-$ sites for each mole of the monosaccharide, as two (2) moles of lactic acid can be found from each mole of sugar converted. The lactic acid and glyceric acid are selectively bound in the resin bed as their lactate and glycerate anions. They can be removed upon washing with an acid solution. Also the basic resins can sometimes be regenerated and reused. The base solution for rendering the resin basic (KOH or NaOH are preferred) was disposed of after it was neutralized.

Batch Experiments

The resins used need to be in the $OH^-$ form. Prior to use, the resins were washed with 1N NaOH solution until the pH is basic and then with water until the pH was neutral to remove unreacted NaOH.

In general, the sugar solution was added and the reaction mixture was stirred at 50° C. for two hours. Reaction occurred and lactic acid was formed and retained on the resin with glyceric acid and other acids in small amounts. Other products were formed in solution.

The resin was filtered off and washed with 0.1N p-toluenesulfonic acid or a mineral acid in a batch process for three hours to recover the lactic acid, glyceric acid and other acids.

The product distribution was analyzed via HPLC (high pressure liquid chromatography).

The resin was regenerated by treatment with 1N NaOH solution followed by water washing.

Continuous Process

A set of three columns in parallel can be used for a continuous process as in FIG. 1. At any given time, one column is regenerating the resin by treatment with NaOH solution and water. In a second column, sugar solution is fed and the reaction takes place over the resin bed to form the C3 products. The third column undergoes recovery of the C3 products from the resin by treatment with an acidic solution.

The resins were obtained from chemical supply companies and were characterized for active site density (meq/ml) by titration prior to use. Initial screening indicated that two resins, AMBERLITE IRA400 (Aldrich) and IRN 78 (Supelco), both polystyrene/divinylbenzene crosslinked materials with tetraalkylammonium hydroxide functionality, were stable in sugar solutions at reaction conditions. These two resins were thus used for all subsequent experiments; active site densities are 2.05 meq/ml for IRN78 and 1.4 meq/ml for IRA 400 resin.

EXAMPLES

Experiments run fall in three categories:

1. The preferred molar ratio as set forth above between the resin active sites and sugar in solution is 2. Besides C3-C4 cleavage, isomerization reactions occurred when AMBERLITE IRA400 was used with either glucose or fructose in solution. AMBERLITE IRN78 leads only to C3 products. In the case of AMBERLITE IRA400, glucose and fructose were observed in the final reaction mixture together along with lactic acid. Treatment of the resin with the acid solution led to partial removal of the products absorbed. Irreversible degradation of some products with the resin occurred to some extent, due probably to condensation reactions catalyzed by the basic sites.

2. When the molar ratio between the resin active sites and sugar in solution was greater than 2, C3-C4 cleavage is observed with total absorption of the sugars from solution. Treatment with acid solution showed formation of lactic acid with small amounts of glyceraldehydes and glyceric acid. The selectivity was better for glucose than for fructose. Use of the regenerated resins gave a significantly lower yield together with isomerization reaction products. Also products of C1-C2 and C2-C3 cleavage were observed.

3. Absorption Studies

At a large excess of resin, immediate adsorption of the sugar from the solution was observed, as expected. Thus, when sugar excess is used, isomerization reaction takes place and equilibrium is reached in 90 minutes.

Experimental

Typical experiments were conducted at 50° C. and consisted of placing 10 ml of fructose or glucose aqueous solution (0.18 M) with 1.2 to 10 ml of resin in a sealed vial, stirring for two hours, filtering the resin, washing with tosylic acid to remove products, and then analyzing the wash solution via HPLC. A summary of these experiments, all conducted at 50° C. for two hours, is given in Table 1.

The carbon balances in all experiments were significantly less than 100%, as sugar absorption and aldol condensation reactions to byproducts result in carbon remaining on the resins after reaction. The "Other" products noted in Table 1 include several compounds that show up in the C6 sugar region on the HPLC, such as formic acid and pyruvaldehyde. These products did not constitute a significant portion of the carbon in the original sugar.

IR studies were conducted on the resins at each step of the experiments, before and after the first reaction, after regeneration, at the end of the second reaction. Retention of the tetraalkylammonium functionality was seen, indicating that active sites in the resins are not destroyed by the buildup of organic residues within the resin. It is believed that the aldol

TABLE 1

Results of initial sugar degradation experiments using ion exchange resins

| Run | Resin/amount (ml resin/10 ml sugar solution) | Feed sugar and concentration (M) | Stoichiometry Resin sites/ 2*mol initial sugar | Glucose | Fructose | Lactic acid | Glyceric acid | Glyceraldehy. | Other[c] | Total sugar conv[a] (%) | Total C3 sel.[b] (% max) | Carbon bal closure (%) |
|---|---|---|---|---|---|---|---|---|---|---|---|---|
| 1 | IRA400/1.2 | Fructose 0.18 | 0.47 | 18.14 | 46.04 | 3.13 | 0 | 0 | 3.39 | 35.82 | 4.37 | 66.50 |
| A1 | IRA400/1.75 | Fructose 0.17 | 0.72 | 22.86 | 19.42 | 13.44 | 0 | 0 | 8.09 | 79.54 | 8.45 | 55.88 |
| B1 | IRA400/1.8 | Fructose 0.18 | 0.70 | 7.9 | 53.69 | 6.54 | 0.82 | 0 | 0 | 38.45 | 9.57 | 65.22 |
| B2 | IRA400/3.2 | Fructose 0.18 | 1.24 | 11.3 | 12.01 | 11.74 | 1.68 | 1.68 | 2.25 | 76.69 | 9.84 | 30.85 |
| A2 | IRA400/8.0 | Fructose 0.17 | 3.29 | 0 | 0 | 119.90 | 7.19 | 21.58 | 0 | 100 | 74.34 | 74.34 |
| B3 | IRA400/8.0 | Fructose 0.17 | 3.29 | 0 | 0 | 84.45 | 10.27 | 21.68 | 9.12 | 100 | 58.2 | 59.72 |
| B4 | IRA400/1.2 | Glucose 0.18 | 0.47 | 51.65 | 21.12 | 3.07 | 0 | 0 | 0 | 27.23 | 5.64 | 74.3 |
| B5 | IRA400/1.8 | Glucose 0.18 | 0.70 | 39.39 | 24.15 | 7.58 | 0 | 0 | 0 | 36.46 | 10.39 | 67.33 |
| B6 | IRA400/3.2 | Glucose 0.18 | 1.24 | 8.02 | 7.93 | 16.85 | 0 | 0 | 0 | 75.46 | 11.16 | 37.51 |
| A3 | IRA400/3.3 | Glucose 0.19 | 1.22 | 3.14 | 2.96 | 47.06 | 5.35 | 10.34 | 14.90 | 96.86 | 32.39 | 44.92 |
| B7 | IRA400/8.0 | Glucose 0.17 | 3.29 | 0 | 0 | 82.71 | 5.59 | 10.06 | 5.60 | 100 | 49.17 | 51.02 |
| A4 | IRA400/8.0 | Glucose 0.19 | 2.94 | 0 | 0 | 106.95 | 0 | 22.46 | 0 | 100 | 64.71 | 64.71 |
| B8 | IRN78/1.0 | Fructose 0.18 | 0.57 | 14.98 | 17.54 | 8.17 | 2.45 | 0 | 4.19 | 67.47 | 7.87 | 38.38 |
| B9 | IRN78/1.5 | Fructose 0.18 | 0.85 | 14.94 | 19.31 | 14.89 | 0 | 0 | 5.67 | 65.74 | 11.32 | 42.83 |
| B10 | IRN78/3.0 | Fructose 0.18 | 1.71 | 0.16 | 0.84 | 44.48 | 6.84 | 0 | 0 | 98.99 | 25.92 | 26.67 |
| A5 | IRN78/3.3 | Fructose 0.17 | 1.99 | 0 | 0 | 95.08 | 10.98 | 6.82 | 6.06 | 100 | 56.44 | 62.75 |
| B11 | IRN78/8.0 | Fructose 0.18 | 4.55 | 0 | 0 | 77.92 | 0 | 0 | 0 | 100 | 38.96 | 38.96 |
| A6 | IRN78/8.0 | Fructose 0.17 | 4.81 | 0 | 0 | 113.91 | 3.60 | 17.99 | 0 | 100 | 67.75 | 67.75 |
| B12 | IRN78/1.0 | Glucose 0.18 | 0.57 | 24.81 | 17.91 | 11.37 | 3.25 | 0 | 2.66 | 57.28 | 12.76 | 50.03 |
| B13 | IRN78/1.5 | Glucose 0.18 | 0.85 | 18.3 | 13.72 | 21.71 | 5.66 | 0 | 1.57 | 67.98 | 20.13 | 45.71 |
| B14 | IRN78/3.0 | Glucose 0.18 | 1.71 | 5.44 | 3.67 | 52.58 | 8.22 | 0 | 0 | 90.9 | 33.44 | 39.5 |
| A7 | IRN78/3.1 | Glucose 0.19 | 1.67 | 0 | 0 | 86.23 | 11.36 | 12.37 | 0 | 100 | 54.98 | 54.98 |
| B15 | IRN78/8.0 | Glucose 0.18 | 4.55 | 0 | 0 | 82.72 | 13.79 | 0 | 0 | 100 | 48.26 | 48.25 |
| A8 | IRN78/8.0 | Glucose 0.19 | 4.31 | 0 | 0 | 106.95 | 9.63 | 19.25 | 0 | 100 | 67.91 | 67.91 |
| C1 | IRN78/8.0 | Fructose 0.12 | 6.82 | 0 | 0 | 96.51 | 10.72 | 0 | 0 | 100 | 53.62 | 53.62 |
| C2 | IRN78/8.0 | Fructose 0.059 | 13.87 | 0 | 0 | 92.31 | 10.25 | 0 | 0 | 100 | 51.28 | 51.28 |
| C3 | IRN78/8.0 | Fructose 0.018 | 45.47 | 0 | 0 | 109.29 | 36.43 | 0 | 0 | 100 | 72.86 | 72.86 |
| C4 | IRN78/8.0 | Glucose 0.12 | 6.82 | 0 | 0 | 82.47 | 10.31 | 0 | 0 | 100 | 46.39 | 46.39 |
| C5 | IRN78/8.0 | Glucose 0.056 | 14.61 | 0 | 0 | 74.87 | 21.39 | 0 | 0 | 100 | 48.13 | 48.13 |
| Experiment in Ethanol | | | | | | | | | | | | |
| C6 | IRN 78/8.0 | Fructose 0.16 | 5.12 | 0 | 0 | 73.31 | 5.64 | 0 | 0 | 100 | 39.48 | 39.48 |

[a]Conversion defined as (mol sugar fed − mol (glucose + fructose) remaining)/mol sugar fed
[b]C3 selectivity defined as mol C3 products formed/(2*(mol sugar fed − mol (glucose + fructose) remaining))

The designations A1, B2, etc. correspond to the different sets of experiments conducted over the course of the development of the present invention. Experiments were performed with at least substoichiometric quantities of resin being present. The first result seen was isomerization of the starting sugars to their C6 counterparts; e.g. fructose isomerizes to glucose. With a significant excess of resin, all sugar was consumed and primarily C3 products are observed in the acid wash solution following the reaction. The maximum molar selectivity to C3 products was approximately 75%, with lactic acid the predominant C3 product and glyceric acid and glyceraldehydes making up the remaining C3 products.

condensation products eventually physically block the pores of the anionic exchange resin, leading to slower and less selective reaction to desired products. The regeneration of the resins was done using NaOH, which would catalyze the aldol reaction even more.

Lowering the reaction temperature to 25° C. resulted in primarily sugar isomerization and little or no cleavage to C3 products. The loss of active site density was less upon regeneration than at 50° C. Higher temperatures would appear to be desirable for enhancing C3 product formation, but the resins are not stable above 60° C. so no reactions were attempted at higher temperatures.

Several washing agents, including toluenesulfonic acid, NH$_4$Cl, NaNO$_3$, and acetonitrile/diluted sulfuric acid mixtures, were examined to probe their ability to remove reaction products, particularly base-catalyzed aldol condensation products. The first three compounds listed above proved to be good at removing the lactic acid and other acids from the resin; unfortunately, the use of these materials did not significantly improve removal of organic condensation products formed in reaction on the resin.

In an effort to limit the adsorption of sugars and the subsequent alkali-catalyzed degradation to C3 products, several anionic exchange resins (from ResinTech, Inc. West Berlin, N.J.) with different porosities and pore size distributions (e.g. macroporous vs. mesoporous) were examined. The different properties of these catalysts affected carbon balances and product distributions mildly, but there were no significant changes in performance or carbon balance over the course of reaction. Finally, basic resins having a trialkyl amine functionality were examined; these catalysts did not give any measurable C3 products upon exposure to glucose under any conditions.

Combined Alkaline Degradation and Hydrogenation

To explore a method to avoid deactivation of the resins and at the same time obtain higher selectivity to desired C3 products, a hydrogenation catalyst was combined with the resin in a batch reaction at 50° C. and 100 psig H$_2$ to facilitate hydrogenation of unsaturated C3 intermediates as they are formed. Two scenarios were examined, one in which a carbon-supported Pt catalyst was placed in the reactor along with the resin and another in which Pt was impregnated and reduced directly on the anionic exchange resin. The resin was impregnated by soaking in a solution of H$_2$PtCl$_6$, washed with water, and then gently reduced in hydrogen at temperatures up to 60° C.

Reaction with Pt/C catalyst added along with anionic exchange resin IRA400 gave the same product distribution as with IRA resin alone.

Results of experiments with Pt-loaded anionic resin are given in Table 2; experiments B3 and B7 from Table 1 are included for comparison. With Pt-loaded resin present in substoichiometric amounts, the main reaction observed is isomerization with minor C3 product formation. Small quantities of products of C1-C2, and C2-C3 cleavage were also observed. With a significant excess of Pt-loaded resin, mainly C3 products are formed. There is clear evidence of hydrogenation activity of the Pt-loaded resin, as glycerol and PG are formed in measurable quantities. Unfortunately, the yield to C3 products is lower than with the resin alone; this is likely because the Pt impregnation leads to partial deactivation of the resin. There is a significant quantity of "Other" products formed, which include formic acid and ethylene glycol as well as pyruvaldehyde and unidentified C6 compounds that could include sorbitol and mannitol.

TABLE 2

Combined alkaline degradation and hydrogenation

| RUN | Resin/ amount (ml resin/ 10 ml sugar solution) | Feed sugar and concentration (M) | Stoichiometry (mol resin/ 2*mol sugar fed) | Feed sugar and concentration (M) | Product molar yields and unreacted sugars remaining (mol product/mole sugar fed) × 100 | | | | | | | | Total sugar conv (%) | Total C3 sel.[b] % max | Carbon bal closure (%) |
|---|---|---|---|---|---|---|---|---|---|---|---|---|---|---|---|
| | | | | | Glucose | Fructose | Lactic acid | Glycer. acid | Glyceraldehyd | GO | PG | Other | | | |
| B3 | IRA400 8.0 | Fructose 0.17 | 3.29 | Fructose 0.17 | 0 | 0 | 84.45 | 10.27 | 21.68 | 0 | 0 | 9.12 | 100 | 58.2 | 59.72 |
| D1 | IRA400-Pt 0.46 | Fructose 0.17 | 0.19 | Fructose 0.17 | 33.03 | 31.01 | 9.5 | 0.34 | 1.12 | 2.8 | 0 | 7.26 | 39.5 | 17.46 | 77.43 |
| D2 | IRA400-Pt 3.21 | Fructose 0.17 | 1.32 | Fructose 0.17 | 6.67 | 0.64 | 49.16 | 3.26 | 1.29 | 4.4 | 1.7 | 22.68 | 93.0 | 29.75 | 43.10 |
| B7 | IRA400 8.0 | Glucose 0.17 | 3.29 | Glucose 0.17 | 0 | 0 | 82.71 | 5.59 | 10.06 | 0 | 0 | 5.60 | 100 | 49.17 | 51.02 |
| D4 | IRA400-Pt 0.46 | Glucose 0.17 | 0.19 | Glucose 0.17 | 53.54 | 7.23 | 3.15 | 0.59 | 0.89 | 0.8 | 0 | 1.12 | 39.2 | 6.89 | 64.40 |
| D5 | IRA400-Pt 3.21 | Glucose 0.17 | 1.32 | Glucose 0.17 | 11.44 | 2.21 | 31.24 | 7.31 | 14.71 | 8.6 | 1.2 | 5.72 | 87.1 | 31.22 | 49.03 |

In summary, addition of Pt catalyst to the anion exchange resin leads to formation of hydrogenation products, but these are formed in relatively small quantities. The hydrogenation activity is offset by partial deactivation of the resin that lowers the overall C3 product yield.

Pentose Sugar Example

Four ml of IRA 400 anion exchange resin was activated using 1.0 M NaOH and then washed with excess water until the wash effluent was pH neutral. Five ml of 0.18 M xylose solution, containing a total of 0.87 mmol of xylose, was added to the washed resin, giving a sugar:resin site molar ratio of approximately 0.1. The sugar solution was contacted with the resin for 2 hr at 50° C. while stirring constantly. Following reaction, the resin was washed with 0.1 M toluenesulfonic acid to remove adsorbed anions. The wash solution was analyzed by high pressure liquid chromatography.

The following products were found in the wash solution:

| | |
|---|---|
| Lactic acid | 0.56 mmol |
| Glycolic acid | 0.15 mmol |

No other liquid products were observed in the reaction and no gas products were formed. The yield of lactic acid was 64%.

It is intended that the foregoing description be only illustrative of the present invention and that the present invention be limited only by the hereinafter appended claims.

We claim:

1. A process for the preparation and purification of lactic acid and glyceric acid in an aqueous solution which comprises:
   (a) reacting an aqueous hexose sugar solution with a solid base at a temperature at least about 30° C. to produce anions of lactic acid and glyceric acid bound to the solid base and unreacted sugars and byproducts in the solution;
   (b) separating the unreacted sugars and byproducts in the solution from the bound lactic acid and glyceric acid anions; and
   (c) contacting the bound lactic acid and glyceric acid anions on the solid base with an aqueous acid solution to produce the lactic acid and glyceric acid in the aqueous solution.

2. A process for the preparation and purification of predominantly lactic acid and glyceric acid in an aqueous solution which comprises:
   (a) reacting an aqueous hexose sugar solution with an anionic ion exchange resin at a temperature between about 30° and 60° C. to produce anions of lactic acid and glyceric acid bound to the anionic ion exchange resin and unreacted sugars and byproducts in the solution;
   (b) separating the unreacted sugars and byproducts in the solution from the bound lactic acid and glyceric acid anions; and
   (c) contacting the bound lactic acid and glyceric acid anions on the anionic exchange column with an aqueous acidic solution to produce purified lactic acid and glyceric acid in the aqueous solution, wherein essentially all of the recovered reaction products in the aqueous solution have three-carbon backbones.

3. The process of claim 2 wherein the process is conducted at atmospheric pressures.

4. The process of any one of claims 1, 2 or 3 wherein the hexose sugar is glucose.

5. The process of any one of claims 1, 2 or 3 wherein the hexose sugar is fructose.

6. The process of any one of claims 1, 2 or 3 wherein the temperature is 50° C.

7. The process of any one of claims 1, 2 or 3 wherein the resin is an anion exchange polystyrene divinylbenzene cross-linked resin.

8. The process of any one of claims 1, 2 or 3 wherein the process is continuous with three (3) columns, one for the reaction in step (a), one for the bound lactic acid and glyceric acid separation in step (b) and one for regeneration of the solid base or anionic exchange resin for reuse.

9. The process of any one of claims 1, 2 or 3 wherein the process is conducted in a sealed vessel.

10. The process of claim 1 or 2 wherein the anions of lactic acid, the anions of glyceric acid, the unreacted sugars, and the byproducts produced in the solution of step (a) are formed with a $C_3$-selectivity of at least about 40 mol. %.

11. The process of claim 10 wherein the $C_3$-selectivity ranges from about 45 mol. % to about 75 mol. %.

12. The process of claim 1 wherein step (a) comprises reacting the aqueous hexose sugar solution with the solid base at a stoichiometric ratio of at least about 1.7, wherein the stoichiometric ratio is defined as the number of hydroxyl equivalents initially present in the solid base divided by twice the moles of hexose sugar initially present in the sugar solution.

13. The process of claim 2 wherein step (a) comprises reacting the aqueous hexose sugar solution with the anionic ion exchange resin at a stoichiometric ratio of at least about 1.7, wherein the stoichiometric ratio is defined as the number of hydroxyl equivalents initially present in the anionic ion exchange resin divided by twice the moles of hexose sugar initially present in the sugar solution.

14. The process of claim 12 or 13 wherein the stoichiometric ratio is at least 2.

15. The process of claim 12 or 13 wherein the stoichiometric ratio ranges from 2 to 50.

* * * * *